US011905242B2

(12) United States Patent
Suzuki

(10) Patent No.: US 11,905,242 B2
(45) Date of Patent: Feb. 20, 2024

(54) METHOD OF PRODUCING PIPERYLENE

(71) Applicant: ZEON CORPORATION, Tokyo (JP)

(72) Inventor: Takahiro Suzuki, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 458 days.

(21) Appl. No.: 17/269,252

(22) PCT Filed: Aug. 29, 2019

(86) PCT No.: PCT/JP2019/033981
§ 371 (c)(1),
(2) Date: Feb. 18, 2021

(87) PCT Pub. No.: WO2020/050137
PCT Pub. Date: Mar. 12, 2020

(65) Prior Publication Data
US 2021/0163380 A1    Jun. 3, 2021

(30) Foreign Application Priority Data
Sep. 5, 2018 (JP) ................. 2018-166100

(51) Int. Cl.
C07C 7/12      (2006.01)
B01D 69/10    (2006.01)
B01D 61/36    (2006.01)
B01D 71/02    (2006.01)

(52) U.S. Cl.
CPC .............. C07C 7/12 (2013.01); B01D 61/362 (2013.01); B01D 69/10 (2013.01); B01D 71/028 (2013.01)

(58) Field of Classification Search
None
See application file for complete search history.

(56) References Cited

U.S. PATENT DOCUMENTS 11,090,617 B2    8/2021   Yamada et al.
2014/0024867 A1  1/2014   Yachi et al.
2018/0200679 A1* 7/2018   Omori ................. B01J 29/40
(Continued)

FOREIGN PATENT DOCUMENTS

CN    105481631 A     4/2016
JP    S4876840 A     10/1973
(Continued)

OTHER PUBLICATIONS

Oct. 21, 2019, International Search Report issued in the International Patent Application No. PCT/JP2019/033981.
(Continued)

Primary Examiner — Tam M Nguyen
(74) Attorney, Agent, or Firm — KENJA IP LAW PC

(57) ABSTRACT

Provided is a method of producing piperylene from a hydrocarbon mixture derived from a petroleum fraction having a carbon number of 5. The hydrocarbon mixture has a piperylene proportional content of not less than 60 mass % and not more than 80 mass % and has a cyclic hydrocarbon proportional content of not less than 20 mass % and not more than 40 mass %. The method of producing piperylene includes a membrane separation step of performing membrane separation of the hydrocarbon mixture using a zeolite membrane to obtain a separated product in which piperylene is enriched.

4 Claims, 2 Drawing Sheets

(56) References Cited

U.S. PATENT DOCUMENTS

2019/0247783 A1\*  8/2019  Omori ................... B01D 53/22
2020/0078743 A1\*  3/2020  Omori ................... C01B 39/40
2020/0199047 A1\*  6/2020  Supronowicz ......... C10G 11/04

FOREIGN PATENT DOCUMENTS

| JP | S4886846 A    | 11/1973 |
| JP | 2002348579 A  | 12/2002 |
| JP | 2013139401 A  |  7/2013 |
| JP | 2015160186 A  |  9/2015 |
| WO | 2012133732 A1 | 10/2012 |
| WO | 2013125661 A1 |  8/2013 |
| WO | 2016121377 A1 |  8/2016 |
| WO | 2017169195 A1 | 10/2017 |

OTHER PUBLICATIONS

Mar. 9, 2021, International Preliminary Report on Patentability issued in the International Patent Application No. PCT/JP2019/033981.

May 19, 2022, the Extended European Search Report issued by the European Patent Office in the corresponding European Patent Application No. 19857954.2.

\* cited by examiner

METHOD OF PRODUCING PIPERYLENE

TECHNICAL FIELD

The present disclosure relates to a method of producing piperylene and, in particular, relates to a method of producing piperylene using a hydrocarbon mixture derived from a petroleum fraction having a carbon number of 5 as a feedstock.

BACKGROUND

Methods using extractive distillation are known as methods for separation and recovery of useful components such as isoprene from a mixture of hydrocarbons having a carbon number of 5, such as a petroleum fraction having a carbon number of 5 that is obtained in the manufacture of ethylene through cracking of naphtha.

In a process of separating and recovering a hydrocarbon such as isoprene from a petroleum fraction having a carbon number of 5 by extractive distillation, attempts are being made to increase the efficiency with which a feedstock is used through effective use of residues.

In one specific example, Patent Literature (PTL) 1 proposes a technique of hydrogenating an extraction residue oil (raffinate) obtained after isoprene is separated from a C5 fraction by extractive distillation, and then returning the resultant hydrogenated product to an ethylene center for use as a gasoline base material or a feedstock for an ethylene cracker.

CITATION LIST

Patent Literature

PTL 1: WO2012/133732A1

SUMMARY

Technical Problem

Of components other than isoprene that are obtained from a petroleum fraction having a carbon number of 5, the usefulness of piperylene (1,3-pentadiene) as a monomer in chemical synthesis has been continuing to attract interest in recent years. There are instances in which piperylene and cyclic hydrocarbons are contained in a hydrocarbon mixture having a specific composition that remains after recovery of a target component from a petroleum fraction having a carbon number of 5.

However, it has been difficult to separate piperylene in high purity from a hydrocarbon mixture having this specific composition by extractive distillation such as described in PTL 1.

Accordingly, an object of the present disclosure is to provide a method of producing piperylene that enables production of high-purity piperylene from a hydrocarbon mixture having a specific composition.

Solution to Problem

Specifically, the present disclosure aims to advantageously solve the problem set forth above, and a presently disclosed method of producing piperylene is a method of producing piperylene from a hydrocarbon mixture that is derived from a petroleum fraction having a carbon number of 5, wherein the hydrocarbon mixture has a piperylene proportional content of not less than 60 mass % and not more than 80 mass % and a cyclic hydrocarbon proportional content of not less than 20 mass % and not more than 40 mass %, and the method comprises a membrane separation step of performing membrane separation of the hydrocarbon mixture using a zeolite membrane to obtain a separated product in which piperylene is enriched. This production method enables production of high-purity piperylene from a hydrocarbon mixture having the specific composition set forth above.

In the presently disclosed method of producing piperylene, the membrane separation step is preferably performed by pervaporation. By performing the membrane separation step by pervaporation, high-purity piperylene can be produced with high sustainability.

Moreover, in the presently disclosed method of producing piperylene, the zeolite membrane is preferably a silylated zeolite membrane that has been silylated in a liquid phase. By using a silylated zeolite membrane that has been silylated in a liquid phase when performing the membrane separation step by pervaporation, high-purity piperylene can be produced with even higher sustainability.

Furthermore, in the presently disclosed method of producing piperylene, it is preferable that the zeolite membrane is a separation membrane including a porous separation layer on a porous support and that the porous support is formed of shirasu porous glass or silicon carbide. When the porous support is formed of shirasu porous glass or silicon carbide, high-purity piperylene can be produced with even higher sustainability.

Advantageous Effect

According to the present disclosure, it is possible to provide a method of producing piperylene that enables production of high-purity piperylene from a hydrocarbon mixture having a specific composition.

DETAILED DESCRIPTION

The following provides a detailed description of embodiments of the present disclosure.

(Method of Producing Piperylene)

The presently disclosed method of producing piperylene is a method of producing piperylene from a hydrocarbon mixture that is derived from a petroleum fraction having a carbon number of 5. Features of the presently disclosed method of producing piperylene are that a hydrocarbon mixture having a piperylene proportional content of not less than 60 mass % and not more than 80 mass % and a cyclic hydrocarbon proportional content of not less than 20 mass % and not more than 40 mass % is used as a feedstock and that a membrane separation step of performing membrane separation of the hydrocarbon mixture using a zeolite membrane to obtain a separated product in which piperylene is enriched is implemented. The following describes, in order, the hydrocarbon mixture serving as a feedstock used in the presently disclosed method of producing piperylene and each step that can be included in the presently disclosed method of producing piperylene.

<Hydrocarbon Mixture Derived From Petroleum Fraction Having Carbon Number of 5>

Features of the hydrocarbon mixture that is derived from a petroleum fraction having a carbon number of 5 and that serves as a feedstock (hereinafter, also referred to as the "hydrocarbon mixture serving as a feedstock") are that the hydrocarbon mixture has a piperylene proportional content of not less than 60 mass % and not more than 80 mass % and a cyclic hydrocarbon proportional content of not less than 20 mass % and not more than 40 mass %. Note that the hydrocarbon mixture serving as a feedstock may optionally contain other components. The proportional content of other components is 20 mass % or less, preferably 5 mass % or less, and may be 0 mass %. Examples of cyclic hydrocarbons include, but are not specifically limited to, cyclopentane, 1-methylcyclobutane, cyclopentene, 1-methylcyclobutene, and cyclopentadiene. Examples of other components include isopentane, isoamylene, n-pentane, and pentene.

Figure 1:
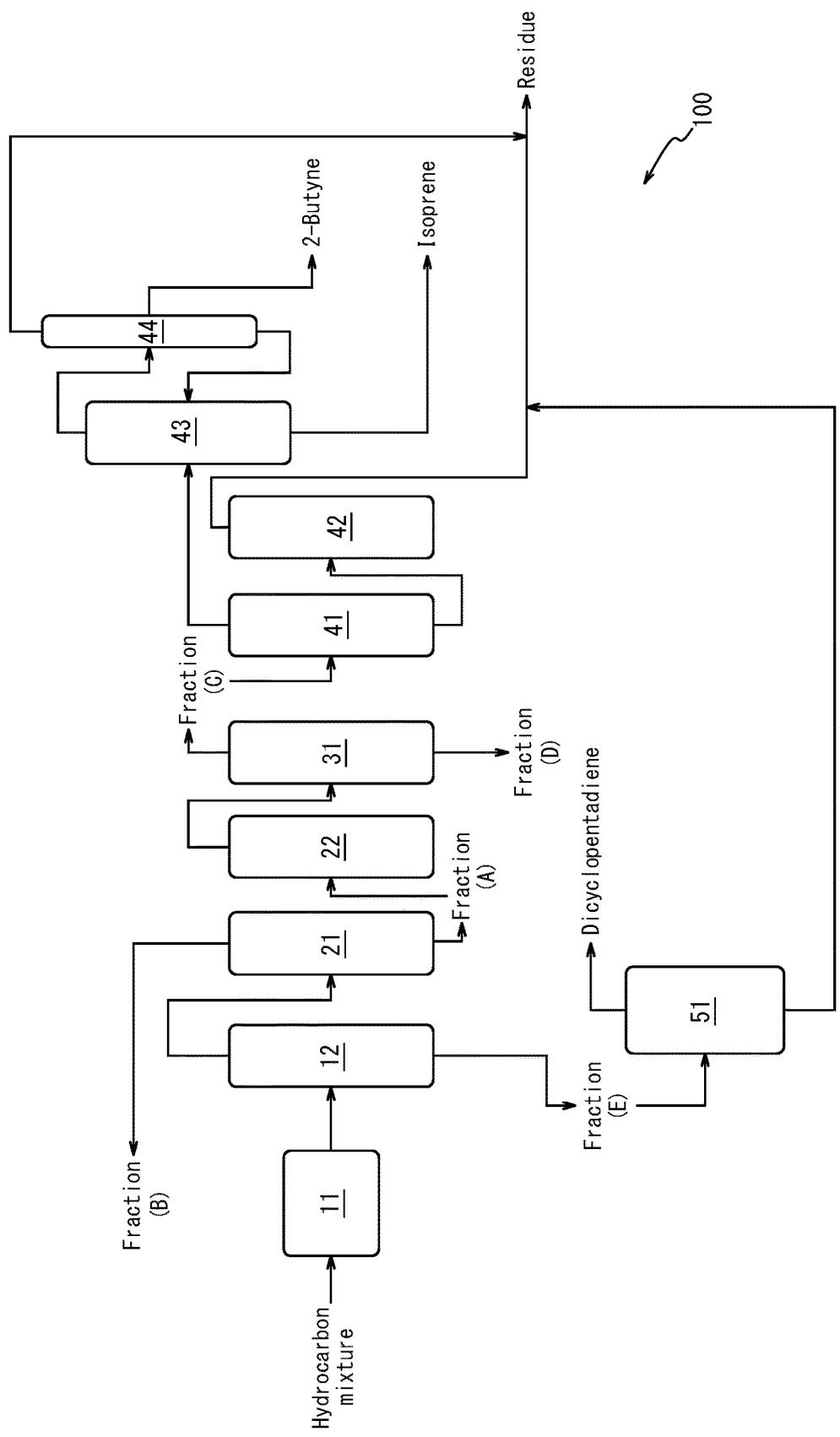
FIG. 1 is an explanatory diagram illustrating schematic configuration of one example of a hydrocarbon production apparatus that can produce a hydrocarbon mixture as a feedstock for use in a hydrocarbon production method conforming with the present disclosure.

The hydrocarbon mixture serving as a feedstock can be produced by any method so long as it satisfies the composition set forth above. For example, the hydrocarbon mixture serving as a feedstock can be obtained using a hydrocarbon production apparatus conforming with a schematic configuration illustrated in FIG. 1. A production apparatus 100 illustrated in FIG. 1 is a production apparatus used to produce mainly dicyclopentadiene, isoprene, and the like from a petroleum fraction having a carbon number of 5. A hydrocarbon mixture that is introduced into the production apparatus as a primary feedstock (i.e., the petroleum fraction having a carbon number of 5) contains isoprene, piperylene, dicyclopentadiene, cyclopentadiene, linear hydrocarbons having a carbon number of 5 and including 1 or fewer carbon-carbon double bonds, branched hydrocarbons having a carbon number of 5 and including 1 or fewer carbon-carbon double bonds, and cyclic hydrocarbons having a carbon number of 5 and including 1 or fewer carbon-carbon double bonds.

The production apparatus 100 includes a dimerizer 11 and a predistillation column 12. Moreover, the production apparatus 100 includes a first extractive distillation column 21 that performs extractive distillation of an extractive distillation target including a pretreated hydrocarbon mixture that flows out from the predistillation column 12, a stripping column 22 that separates an extractant from a fraction (A) that flows out from the bottom of the first extractive distillation column 21, and a first distillation column 31 that performs distillation of a fraction obtained through separation of the extractant from the fraction (A) in the stripping column 22.

The production apparatus 100 also includes, as an isoprene purification section that purifies a fraction (C) that flows out from the top of the first distillation column 31 to obtain high-purity isoprene, a second extractive distillation column 41 into which the fraction (C) flows, a stripping column 42 that separates a fraction that flows out from the bottom of the second extractive distillation column 41 into a residue and an extractant, a second distillation column 43 that performs distillation of a fraction that flows out from the top of the second extractive distillation column 41, and a purification column 44 that purifies a fraction that flows out from the top of the second distillation column 43.

Furthermore, the production apparatus 100 includes a distillation column 51 as a dicyclopentadiene purification section that purifies a fraction (E) that flows out from the bottom of the predistillation column 12 to obtain high-purity dicyclopentadiene.

In a production apparatus having a configuration such as set forth above, the petroleum fraction having a carbon number of 5 firstly undergoes dimerization of cyclopentadiene contained in the petroleum fraction having a carbon number of 5 in the dimerizer 11 to obtain a mixture containing dicyclopentadiene. The obtained mixture containing dicyclopentadiene is distilled in the predistillation column 12 to obtain a pretreated mixture from the top of the predistillation column 12 and a fraction (E) in which dicyclopentadiene is enriched from the bottom of the predistillation column 12. The pretreated mixture is subjected to extractive distillation in the first extractive distillation column 21 to obtain a fraction (A) in which isoprene and piperylene are enriched and a fraction (B) in which linear hydrocarbons and branched hydrocarbons having lower solubility than isoprene and piperylene in an extractant used in the extractive distillation are enriched. The extractant is separated from the obtained fraction (A) in the stripping column 22. Thereafter, the fraction (A) from which the extractant has been removed is distilled in the first distillation column 31 to obtain a fraction (C) in which isoprene is enriched and a fraction (D) in which piperylene is enriched. Note that the fraction (C) can be separated into isoprene, 2-butyne, and the like through the second extractive distillation column 41, the second distillation column 43, the purification column 44, and so forth. The fraction (D) obtained in the first distillation column 31 can correspond to a hydrocarbon mixture having a piperylene proportional content of not less than 60 mass % and not more than 80 mass % and a cyclic hydrocarbon proportional content of not less than 20 mass % and not more than 40 mass %.

<Membrane Separation Step>

In the membrane separation step, the hydrocarbon mixture that is derived from a petroleum fraction having a carbon number of 5 and that satisfies the previously described composition is subjected to membrane separation using a zeolite membrane to obtain a separated product in which piperylene is enriched. By performing membrane separation of the hydrocarbon mixture having the specific composition using a zeolite membrane, the piperylene concentration in the resultant separated product can be dramatically increased.

No specific limitations are placed on the membrane separation step so long as membrane separation is performed at least once in a single membrane separation step, and membrane separation can be performed a plurality of times. By performing membrane separation a plurality of times in a single membrane separation step, the resultant piperylene concentration can be further increased. Note that the upper limit for the number of times membrane separation is performed in a single membrane separation step is preferably 3 times, and more preferably 2 times from a viewpoint of production efficiency.

Moreover, the membrane separation step can be performed by vapor permeation, pervaporation, or the like. In particular, it is preferable that the membrane separation step is performed by pervaporation. The term "pervaporation" as used in the present specification refers to a method in which a liquid hydrocarbon mixture is supplied to a zeolite membrane for which a reduced pressure condition is set at the permeate side, and a portion of the liquid hydrocarbon mixture is caused to diffuse and permeate into the zeolite membrane, and thereby reach the permeate side of the zeolite membrane where it evaporates to obtain a separated product as a gas. By performing the membrane separation step by pervaporation, it is possible to inhibit blocking of the zeolite membrane and the presence of residual adhered material on the surface of the zeolite membrane. More specifically, since there is a flow of the liquid hydrocarbon mixture at the supply side surface of the zeolite membrane where the liquid hydrocarbon mixture comes into contact with the zeolite membrane, it is possible to effectively inhibit the retentate from accumulating inside pores of the zeolite membrane, and thereby blocking the zeolite membrane, and also to effectively inhibit the retentate or the like from remaining at the membrane surface. The adoption of pervaporation, therefore, makes it possible to lengthen the period of time that the zeolite membrane can be used without replacement, cleaning, regeneration, or the like, and thus enables production of high-purity piperylene with high sustainability.

In a case in which the membrane separation step is performed by pervaporation, the pressure applied to the liquid hydrocarbon mixture at the supply side and the temperature to which the liquid hydrocarbon mixture is heated at the supply side can be controlled as appropriate such that the hydrocarbon mixture does not vaporize at the supply side. In particular, the heating temperature of the hydrocarbon mixture at the supply side is preferably 100° C. or lower, more preferably 80° C. or lower, and particularly preferably 75° C. or lower. The pressure can be controlled as appropriate based on the temperature condition such that the hydrocarbon mixture does not vaporize, but the pressure difference between the supply side and the permeate side is preferably not less than 200 kPa and not more than 1.1 MPa, and more preferably not less than 200 kPa and not more than 600 kPa. When the heating temperature is not higher than any of the upper limits set forth above, membrane separation can be performed efficiently without the need to apply an excessively high pressure to the hydrocarbon mixture at the supply side. Moreover, the heating temperature of the hydrocarbon mixture at the supply side is preferably 10° C. or higher, and more preferably 15° C. or higher. When the heating temperature is not lower than any of the lower limits set forth above, the permeation flux in the membrane separation step can be increased, and piperylene can be efficiently produced.

The zeolite membrane used in the membrane separation step can be produced according to a known method described in WO2016/121377A1 using a porous body formed of glass such as shirasu porous glass; a ceramic such as silicon dioxide (silica), silicon carbide, or titania; or a metal such as stainless steel as a porous support that is a porous body including a plurality of pores. Of these porous bodies, a porous body formed of shirasu porous glass or silicon carbide is preferable. When the porous support is formed of shirasu porous glass or silicon carbide, high-purity piperylene can be produced with even higher sustainability. The porous supports listed above can suitably be used to produce piperylene as they tend not to cause a solid acid reaction even upon coming into contact with piperylene, which is a diolefin. The zeolite membrane is preferably a separation membrane including a porous separation layer that contains an MFI-type zeolite on the porous support.

Moreover, the zeolite membrane used in the membrane separation step is preferably a zeolite membrane that has undergone silylation treatment using a silylating agent. The silylating agent may be hexamethyldisilazane, trimethylchlorosilane, dimethyldichlorosilane, or the like. Moreover, the silylating agent preferably does not include a halogen atom and is particularly preferably hexamethyldisilazane among the silylating agents listed above. This is because degradation of the zeolite membrane due to the silylation treatment can be inhibited when the silylating agent does not include a halogen atom. The method of silylation treatment is not specifically limited and may be gas-phase silylation that involves bringing the zeolite membrane into contact with a silylating agent that is in a vapor state or liquid-phase silylation that involves bringing the zeolite membrane into contact with a silylating agent that is in a liquid state.

More specifically, the gas-phase silylation involves implementing a vaporization step of vaporizing a silylating agent by a known vaporization method such as bubbling and a vapor contact step of bringing the zeolite membrane into contact with vapor of the silylating agent obtained in the vaporization step. The contact time in the gas-phase silylation can be not less than 12 hours and not more than 24 hours, for example.

Moreover, the liquid-phase silylation involves implementing an immersion step of immersing the zeolite membrane in a liquid that contains a silylating agent. The liquid containing a silylating agent may be a liquid composed of only a liquid silylating agent or may be a solution containing a silylating agent and a solvent. A known solvent can be used as the solvent without any specific limitations. The immersion time in the liquid-phase silylation can be not less than 12 hours and not more than 24 hours, for example.

In silylation treatment of the zeolite membrane, it is preferable that liquid-phase silylation is adopted as the method of silylation treatment. By implementing the membrane separation step using a silylated zeolite membrane that has been silylated in a liquid phase, it is possible to lengthen the period of time for which the zeolite membrane can be used without replacement, cleaning, regeneration, or the like, and thus it is possible to produce high-purity piperylene with high sustainability.

<Recovery Step>

The separated product that is separated in the membrane separation step and is present at the permeate side of the zeolite membrane can be recovered by a known method such as cooling. Note that even in a situation in which the previously described pervaporation or vapor permeation is adopted in the membrane separation step, the separated product present at the permeate side of the zeolite membrane is present in a gaseous state and can be recovered as a liquid through condensation by cooling. The piperylene concentration in the separated product that is recovered in the recovery step is preferably 90 mass % or more, and more preferably 94 mass % or more.

Moreover, the cyclic hydrocarbon concentration in the separated product is preferably 10 mass % or less, more preferably 6 mass % or less, and even more preferably 1 mass % or less.

EXAMPLES

The following provides a more detailed description of the present disclosure through examples. However, the present disclosure is not limited to these examples. Note that pressures are gauge pressures unless otherwise specified.

Example 1

A membrane separation step was performed by pervaporation with respect to a hydrocarbon mixture (a) having a piperylene proportional content of not less than 62 mass % and not more than 65 mass % and a cyclic hydrocarbon proportional content of not less than 35 mass % and not more than 38 mass % using a liquid-phase silylated zeolite membrane that was obtained as described below.

<Preparation of Zeolite Membrane>

<<Preparation of Aqueous Sol for Seed Crystals>>

A magnetic stirrer was used to mix 152.15 g of tetrapropylammonium hydroxide aqueous solution of 22.5 mass % in concentration (produced by Tokyo Chemical Industry Co., Ltd.; 34.23 gin terms of tetrapropylammonium hydroxide as a structure directing agent) and 48.44 g of ultrapure water. In addition, 99.41 g of tetraethoxysilane (produced by Sigma-Aldrich) was added as a silica source and was mixed therewith at room temperature for 70 minutes by the magnetic stirrer to prepare an aqueous sol for seed crystal production.

<<Production of Zeolite Seed Crystals>>

The aqueous sol for seed crystals was loaded into a stainless steel pressure-resistant vessel including a fluororesin inner cylinder, and then a reaction (hydrothermal synthesis) was carried out for 48 hours in a 130° C. hot-air dryer. Next, solid-liquid separation of the resultant reaction liquid was performed for 30 minutes by centrifugal separation in a centrifugal separator (4,000 rpm), and solid content was recovered. The recovered solid content was dried in an 80° C. thermostatic dryer for 12 hours, and then the resultant dry solid was ground in a mortar to obtain zeolite seed crystals. The obtained zeolite seed crystals were confirmed to have an MFI-type structure by X-ray diffraction measurement. Note that the zeolite seed crystals had an average particle diameter of 400 nm.

<<Adhesion of Zeolite Seed Crystals to Porous Support>>

Shirasu porous glass (produced by SPG Technology Co., Ltd.; pore diameter: 1.4 μm; external diameter: 10 mm; length L: 100 mm; indicated by "SPG" in the table) was washed with acetone, subsequently dried, and then immersed in ultrapure water for 10 minutes. After this immersion in ultrapure water, 0.05 g of the zeolite seed crystals obtained as described above were rubbed onto the outer surface of the wet porous support and were dried in an 80° C. dryer for 12 hours to adhere the zeolite seed crystals to the surface of the porous support.

<<Preparation of Aqueous Sol for Porous Separation Layer>>

A magnetic stirrer was used to mix 4.99 g of tetrapropylammonium hydroxide aqueous solution of 22.5 mass % in concentration (produced by Tokyo Chemical Industry Co., Ltd.; 1.12 gin terms of tetrapropylammonium hydroxide as structure directing agent), 0.74 g of tetrapropylammonium bromide (produced by Wako Pure Chemical Industries, Ltd.) as a structure directing agent, and 238.79 g of ultrapure water for 10 minutes at room temperature. In addition, 6.71 g of tetraethoxysilane (produced by Sigma-Aldrich) was added as a silica source and was mixed therewith at room temperature for 60 minutes using the magnetic stirrer to prepare an aqueous sol for porous separation layer formation. The composition of the aqueous sol, by molar ratio, was tetraethoxysilane:tetrapropylammonium hydroxide:tetrapropyl ammonium bromide:water=1:0.2:0.1:419.

<<Formation of Porous Separation Layer>>

The aqueous sol for a porous separation layer obtained as described above was loaded into a stainless steel pressure-resistant vessel. Next, the porous support having the zeolite seed crystals adhered thereto was immersed in the aqueous sol for a porous separation layer, and a reaction (hydrothermal synthesis) was carried out for 24 hours in a 185° C. hot-air dryer to form a porous separation layer on the porous support. The porous support having the porous separation layer formed thereon was subjected to two repetitions of boil washing for 1 hour using distilled water as a washing liquid. Thereafter, the porous support having the porous separation layer formed thereon was dried for 12 hours using an 80° C. thermostatic dryer. Next, firing was performed to remove the structure directing agents (tetrapropylammonium hydroxide and tetrapropylammonium bromide) contained in the porous separation layer, and thereby obtain a separation membrane. The firing conditions were as follows.

Heating rate: 0.25° C./minute

Firing temperature: 500° C.

Firing time (hold time): 20 hours

Cooling rate: 0.38° C./minute

The thickness of the porous separation layer in the resultant separation membrane was measured. Moreover, X-ray diffraction measurement of the porous separation layer was performed to obtain an X-ray diffraction pattern. As a result, it was confirmed that the porous separation layer contained an MFI-type zeolite based on the obtained X-ray diffraction pattern.

<<Silylation Step>>

Hexamethyldisilazane was used as a silylating agent. The separation membrane obtained as described above was immersed in hexamethyldisilazane (normal temperature liquid) at normal temperature (JIS Z 8703:1983) for 24 hours, was subsequently pulled out of the hexamethyldisilazane, and was then dried at 150° C. for 4 hours to obtain a silylated zeolite membrane that had been silylated in a liquid phase.

<Membrane Separation Step>

Figure 2:
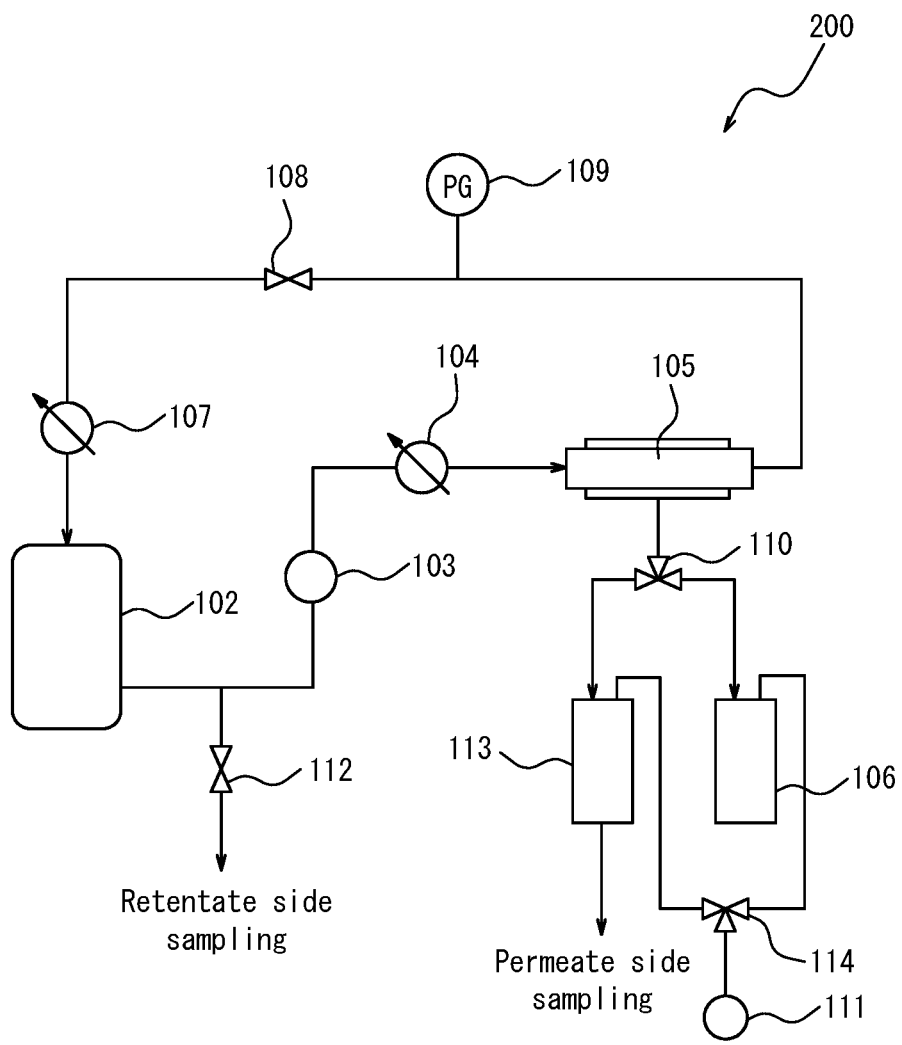
FIG. 2 is an explanatory diagram illustrating schematic configuration of one example of a test apparatus used for testing a hydrocarbon production method conforming with the present disclosure.

The silylated zeolite membrane obtained as described above was used to perform membrane separation using a test apparatus 200 having a schematic configuration such as illustrated in FIG. 2. Note that membrane separation was performed twice in the membrane separation step. In the following description, the first time membrane separation was performed is referred to as "first membrane separation" and the second time membrane separation was performed is referred to as "second membrane separation".

[Test Apparatus]

The test apparatus 200 illustrated in FIG. 2 includes a feedstock tank 102, a liquid feed pump 103, a first heat exchanger 104, a separator 105, and a second heat exchanger 107. The separator 105 is configured by setting up the silylated zeolite membrane obtained as described above in a circular tube. The test apparatus 200 illustrated in FIG. 2 also includes a cold trap 106 and a sampling cold trap 113 that are connected to the separator 105 via a three-way valve 110, and a vacuum pump 111 that is connected downstream of the cold trap 106 and the cold trap 113 via a three-way valve 114. Moreover, the test apparatus 200 includes a sampling valve 112 between the feedstock tank 102 and the liquid feed pump 103, and a back pressure valve 108 and a pressure gauge 109 downstream of the separator 105.

In the test apparatus 200 illustrated in FIG. 2, a feedstock that has been loaded into the feedstock tank 102 is fed to the first heat exchanger 104 by the liquid feed pump 103. In a case in which pervaporation (abbreviated as "PV" in the table) is performed in the membrane separation step, the feedstock can be heated to a temperature that is within a range with which the feedstock does not vaporize under the pressure condition at the retentate side. Also note that heat exchange may not be performed in the first heat exchanger 104 (i.e., the feedstock may not be heated). Moreover, in a case in which the membrane separation step is performed by vapor permeation (abbreviated as "VP" in the table), rather than by pervaporation, the feedstock can be heated by the first heat exchanger 104 to a temperature such that the feedstock vaporizes under the pressure condition at the retentate side. The feedstock is fed to the separator 105 as a liquid phase and then undergoes separation (membrane separation) of components by the separator 105 including the silylated zeolite membrane. In the test apparatus 200, the permeate side of the silylated zeolite membrane is placed in a reduced pressure state by the vacuum pump 111, and a permeate that has passed through the silylated zeolite membrane is fed to the cold trap 106 or the sampling cold trap 113 that is connected via the three-way valve 110. On the other hand, a retentate that has not passed through the silylated zeolite membrane included in the separator 105 is cooled by the second heat exchanger 107 and is returned to the feedstock tank 102. Note that back pressure in the test apparatus 200 is adjusted by the back pressure valve 108 and the pressure gauge 109 provided downstream of the separator 105. In the test apparatus 200, a permeate that has passed through the silylated zeolite membrane included in the separator 105 can be extracted as a permeate side sample through switching of the three-way valves 110 and 114.

[Membrane Separation]

The first membrane separation was implemented as follows using the test apparatus 200 illustrated in FIG. 2. Specifically, the hydrocarbon mixture (a) satisfying the specific composition described above was first loaded into the feedstock tank 102 and a degassing operation was performed three times. Thereafter, a feedstock circulation process was initiated in which the hydrocarbon mixture (a) was fed to the separator 105 as a liquid phase by the liquid feed pump 103, via the first heat exchanger 104, which was heated to 70° C., and was then condensed by the second heat exchanger 107 and returned to the feedstock tank 102. After the feedstock circulation process had been initiated, operation was continued until the temperature of the system reached a steady state. Once the temperature of the system reached a steady state, the back pressure valve 108 was used to increase the pressure at the retentate side to 180 kPa, and the vacuum pump 111 was operated to reduce the pressure at the permeate side (region at permeate side of silylated zeolite membrane inside separator 105, cold trap 106, and cold trap 113) to −100 kPa. After a stable temperature and pressure had been confirmed in the system, the three-way valve 110 at the permeate side was opened to start the first membrane separation. In other words, the first membrane separation was performed under conditions of a temperature of 70° C. and a pressure difference between the retentate side and the permeate side of 280 kPa.

Extraction of a permeate side sample was started after 5 minutes had passed from the start of the first membrane separation. Specifically, the three-way valves 110 and 114 were used to switch the flow path at the permeate side from the cold trap 106 to the sampling cold trap 113, and a permeate side sample was extracted by collection as a condensate in the sampling cold trap 113. The sampling time during this was set as 10 minutes.

Next, the second membrane separation was implemented. In implementation of the second membrane separation, the permeate side sample (condensate) that had been obtained in the first membrane separation was first loaded into the feedstock tank 102 of the test apparatus 200. The second membrane separation was then performed and a permeate side sample was obtained in the same way as in the first membrane separation with the exception that the first heat exchanger 104 was not heated, the start of sampling was set as a point after 55 minutes had passed, and the sampling time was set as 20 minutes.

The weight of the permeate side sample obtained in each of the first and second membrane separations was weighed, and the piperylene concentration in the permeate side sample was measured by a gas chromatograph. As a result, the piperylene concentration in the sample obtained through the first membrane separation was confirmed to be 95 mass %, and the piperylene concentration in the sample obtained through the second membrane separation was confirmed to be 98 mass %. Moreover, the cyclic hydrocarbon concentration in the sample obtained through the second membrane separation was 0.5 mass %.

Note that the measurement conditions in measurement of the piperylene concentration using the gas chromatograph were as follows.
Apparatus: GC-2025 produced by Shimadzu Corporation
Column: InertCap 60m produced by Agilent Technologies, Inc.
Column temperature: 40° C. to 250° C.
Injection temperature: 250° C.
Carrier gas: Nitrogen
Detector: Flame ionization detector Comparative Example 1

Simulation software (Aspen Plus produced by Aspen Technology Inc.) was used to perform a simulation for a case in which piperylene is produced through separation of the same hydrocarbon mixture (a) as in Example 1 by extractive distillation rather than by membrane separation. The simulation conditions were as follows.
Reflux ratio: 5
Number of stages: 100 stages
Feed stage: $20^{th}$ stage
D/F: 0.1
Feed rate: 1 kg/hr
Temperature: 70° C.
Pressure: 130 kPaG
The simulation results were as follows.
(1) Distillate side
Amount of distillate: 0.1 kg/hr
Temperature: 41° C.
Pressure: 0 kPaG
Piperylene concentration in distillate: 76 mass %
(2) Bottom liquid side
Amount of bottom liquid: 0.9 kg/hr
Temperature: 56° C.
Pressure: 55 kPaG
Piperylene concentration in bottom liquid: 64 mass %

The following can be seen upon comparison of Example 1 and Comparative Example 1. It is clear from Example 1 that the separated product obtained through membrane separation of the hydrocarbon mixture satisfying the specific composition had a significantly higher piperylene concentration. In contrast, it is thought based on Comparative Example 1 that a separated product having a sufficiently high piperylene concentration cannot be obtained in a situation in which piperylene is separated from the hydrocarbon mixture satisfying the specific composition by extractive distillation instead of membrane separation.

Example 2

A separation factor and a separation performance maintenance rate were calculated as follows for a sample obtained by the first membrane separation in Example 1. The results are shown in Table 1.

<Calculation Method of Separation Factor and Separation Performance Maintenance Rate>

First, the permeation flux F was calculated using the following equation (I). Moreover, the separation factor α was calculated using the following equation (II). The product of the separation factor a and the permeation flux F (i.e., F×α) was calculated, and separation performance was evaluated based on this value. A larger value for F×α indicates better separation performance. In addition, the value of F×α at 10 minutes after the start of the test was taken to be 100%, and the value of F×α at each subsequent sampling time was calculated as a proportion relative thereto to determine a separation performance maintenance rate. A higher value for the separation performance maintenance rate indicates that high-purity piperylene can be produced with higher sustainability.

$$F[kg/(m^2 \cdot hr)] = W/(A \times t) \quad (I)$$

$$\alpha = (Y_p/Y_c)/(X_p/X_c) \quad (II)$$

In equation (I), W is the mass [kg] of a component that has passed through the separation membrane, A is the effective area [m$^2$] of the separation membrane, and t is the processing time [hr]. In equation (II), $X_p$ is the proportional content [mol %] of piperylene in the feedstock, $X_c$ is the proportional content [mol %] of cyclic hydrocarbons in the feedstock, $Y_p$ is the proportional content [mol %] of piperylene in a permeate side sample, and $Y_c$ is the proportional content [mol %] of cyclic hydrocarbons in the permeate side sample.

Note that in collection of permeate side samples, the sampling time was set as 10 minutes as described below. Values for points 10 minutes, 1 hour, 2 hours, 3 hours, 4 hours, and 5 hours after the start of the test were calculated using samples collected with each of these points as a midpoint in the sampling time of 10 minutes.

Example 3

Example 3 is an example in which the membrane separation step was performed using a silylated membrane obtained through silylation in a gas phase. Specifically, the same operations as in Example 1 were performed up to the first membrane separation with the exception that silylation was performed in a gas phase rather than in a liquid phase in the "Silylation step" of "Preparation of zeolite membrane". The same measurements and evaluations as in Example 2 were performed with respect to samples obtained through the first membrane separation. The results are shown in Table 1. It was confirmed that the porous separation layer of the separation membrane contained an MFI-type zeolite as a result of X-ray diffraction measurement of the porous separation layer.

<Gas-Phase Silylation Step>

In the gas-phase silylation, vapor of hexamethyldisilazane that had been vaporized by nitrogen bubbling was brought into contact with a separation membrane obtained through the same steps as in "Formation of porous separation layer" in Example 1 for 24 hours. Thereafter, 4 hours of drying was performed at 150° C. to obtain a silylated zeolite membrane that had been silylated in a gas phase.

Example 4

Example 4 is an example in which the membrane separation step was performed by vapor permeation (VP). Specifically, the same operations as in Example 1 were performed up to the first membrane separation with the exception that the "Silylation step" in "Preparation of zeolite membrane" was not performed and the pressure at the retentate side was set as 140 kPa in "Membrane separation" of the "Membrane separation step" such that a gaseous hydrocarbon mixture (a) was brought into contact with the surface at the retentate side of the zeolite membrane. The same measurements and evaluations as in Example 2 were performed with respect to samples obtained through the first membrane separation. The results are shown in Table 1.

Example 5

The membrane separation step was implemented with respect to a hydrocarbon mixture (a-1) having a piperylene proportional content of not less than 60 mass % and not more than 80 mass % and a cyclic hydrocarbon proportional content of not less than 20 mass % and not more than 40 mass %. A separation membrane formed by using a porous support other than shirasu porous glass as the porous support to which zeolite seed crystals were adhered was adopted as the separation membrane used in the membrane separation step. Specifically, the same operations as in Example 1 were performed with the exception that silicon carbide (pore diameter: 1.4 μm internal diameter: 12 mm; length L: 100 mm; indicated by "SiC" in the table) was used instead of shirasu porous glass as a porous support in "Adhesion of zeolite seed crystals to porous support" of "Preparation of zeolite membrane", and the temperature of the hot-air dryer was set as 125° C. instead of 185° C. in "Formation of porous separation layer". The same measurements and evaluations as in Example 2 were performed with respect to samples obtained through the first membrane separation. The results are shown in Table 1.

It was confirmed that the porous separation layer of the separation membrane contained an MFI-type zeolite as a result of X-ray diffraction measurement of the porous separation layer.

Example 6

The membrane separation step was implemented with respect to a hydrocarbon mixture (a-1) having a piperylene proportional content of not less than 60 mass % and not more than 80 mass % and a cyclic hydrocarbon proportional content of not less than 20 mass % and not more than 40 mass %.

A separation membrane formed by using a porous support other than shirasu porous glass as the porous support to which zeolite seed crystals were adhered and by not performing silylation of the zeolite membrane was adopted as the separation membrane used in the membrane separation step. Specifically, the same operations as in Example 1 were performed with the exception that silicon carbide was used instead of shirasu porous glass in "Adhesion of zeolite seed crystals to porous support" of "Preparation of zeolite membrane", the temperature of the hot-air dryer was set as 125° C. instead of 185° C. in "Formation of porous separation layer", and the "Silylation step" was not implemented. The same measurements and evaluations as in Example 2 were performed with respect to samples obtained through the first membrane separation. The results are shown in Table 1.

It was confirmed that the porous separation layer of the separation membrane contained an MFI-type zeolite as a result of X-ray diffraction measurement of the porous separation layer.

TABLE 1

|  |  |  |  | Example 2 | Example 3 | Example 4 | Example 5 | Example 6 |
|---|---|---|---|---|---|---|---|---|
| Zeolite membrane | Seed crystals | Average particle diameter (nm) |  | 400 | 400 | 400 | 400 | 400 |
|  |  | Porous support |  | SPG | SPG | SPG | SiC | SiC |
|  |  | Silylation method |  | Liquid phase | Gas phase | None | Liquid phase | None |
| Membrane separation step |  | Type |  | PV | PV | VP | PV | PV |
| Separation performance | Sampling time | After 10 minutes | Separation factor α (—) | 15.3 | 14.7 | 15.0 | 4.9 | 1.8 |
|  |  |  | Permeation flux F (kg/($m^2$ · hr)) | 2.60 | 3.82 | 2.58 | 1.49 | 3.57 |
|  |  |  | F × α (kg/($m^2$ · hr)) | 39.7 | 56.1 | 38.6 | 7.3 | 6.5 |
|  |  | After 1 hour | Separation factor α (—) | 15.3 | 14.5 | 15.8 | 6.4 | 2.3 |
|  |  |  | Permeation flux F (kg/($m^2$ · hr)) | 2.59 | 3.74 | 1.80 | 1.18 | 2.38 |
|  |  |  | F × α (kg/($m^2$ · hr)) | 39.5 | 54.3 | 28.5 | 7.6 | 5.5 |
|  |  |  | Maintenance rate (%) | 99.6 | 96.8 | 73.8 | 104.4 | 84.4 |
|  |  | After 2 hours | Separation factor α (—) | 15.5 | 14.8 | 16.3 | 7.0 | 2.3 |
|  |  |  | Permeation flux F (kg/($m^2$ · hr)) | 2.43 | 3.35 | 1.57 | 1.04 | 2.10 |
|  |  |  | F × α (kg/($m^2$ · hr)) | 37.7 | 49.8 | 25.6 | 7.2 | 4.8 |
|  |  |  | Maintenance rate (%) | 94.9 | 88.8 | 66.3 | 99.4 | 74.3 |
|  |  | After 3 hours | Separation factor α (—) | 15.7 | 15.0 | 16.6 | 7.3 | 2.6 |
|  |  |  | Permeation flux F (kg/($m^2$ · hr)) | 2.29 | 3.05 | 1.29 | 1.04 | 1.71 |
|  |  |  | F × α (kg/($m^2$ · hr)) | 35.9 | 45.8 | 21.3 | 7.6 | 4.5 |
|  |  |  | Maintenance rate (%) | 90.6 | 81.6 | 55.2 | 104.5 | 68.7 |
|  |  | After 4 hours | Separation factor α (—) | 15.8 | 15.1 | 16.7 | 7.6 | 2.7 |
|  |  |  | Permeation flux F (kg/($m^2$ · hr)) | 2.17 | 2.82 | 1.20 | 0.96 | 1.54 |
|  |  |  | F × α (kg/($m^2$ · hr)) | 34.4 | 42.7 | 20.1 | 7.4 | 4.1 |
|  |  |  | Maintenance rate (%) | 86.8 | 76.1 | 51.9 | 100.9 | 62.8 |
|  |  | After 5 hours | Separation factor α (—) | 16.0 | 15.1 | 16.8 | 7.8 | 2.7 |
|  |  |  | Permeation flux F (kg/($m^2$ · hr)) | 2.06 | 2.53 | 1.13 | 0.91 | 1.45 |
|  |  |  | F × α (kg/(nr · hr)) | 33.1 | 38.2 | 19.0 | 7.1 | 3.9 |
|  |  |  | Maintenance rate (%) | 83.3 | 68.2 | 49.1 | 97.6 | 59.5 |

It is clear upon comparison of Examples 2 and 3 with Example 4 that it was possible to cause the separation performance maintenance rate in the membrane separation step to decrease more gradually by adopting a silylated zeolite membrane as a separation membrane and adopting pervaporation in the membrane separation step. It is also clear upon comparison of Examples 2 to 6 that it was possible to cause the separation performance maintenance rate to decrease even more gradually in a situation in which a silylated zeolite membrane that had been silylated in a liquid phase was used, in particular, as compared to a situation in which a zeolite membrane that had not been silylated or a zeolite membrane that had been silylated in a gas phase was used.

INDUSTRIAL APPLICABILITY

According to the present disclosure, it is possible to provide a method of producing piperylene that enables production of high-purity piperylene from a hydrocarbon mixture having a specific composition.

REFERENCE SIGNS LIST

11 dimerizer
12 predistillation column
21 first extractive distillation column
22 stripping column
31 first distillation column
41 second extractive distillation column
42 stripping column
43 second distillation column
44 purification column
51 distillation column
100 production apparatus
102 feedstock tank
103 liquid feed pump
104 first heat exchanger 105 separator
106 cold trap
107 second heat exchanger
108 back pressure valve
109 pressure gauge
110, 114 three-way valve
111 vacuum pump
112 sampling valve
113 sampling cold trap
200 test apparatus

The invention claimed is:

1. A method of producing piperylene from a hydrocarbon mixture that is derived from a petroleum fraction having a carbon number of 5, wherein
the hydrocarbon mixture has a piperylene proportional content of not less than 60 mass % and not more than 80 mass % and a cyclic hydrocarbon proportional content of not less than 20 mass % and not more than 40 mass %, and
the method comprises a membrane separation step of performing membrane separation of the hydrocarbon mixture using a zeolite membrane, having a silyl group originated from a silylating agent including at least one of hexamethyldisilazane, trimethylchlorosilane, and dimethyldichlorosilane, to obtain a separated product in which piperylene is enriched.

2. The method of producing piperylene according to claim 1, wherein the membrane separation step is performed by pervaporation.

3. The method of producing piperylene according to claim 2, wherein the zeolite membrane is a silylated zeolite membrane that has been silylated in a liquid phase.

4. The method of producing piperylene according to claim 1, wherein the zeolite membrane is a separation membrane that includes a porous separation layer on a porous support, and the porous support is formed of shirasu porous glass or silicon carbide.

* * * * *